US007499521B2

(12) United States Patent
Wang et al.

(10) Patent No.: US 7,499,521 B2
(45) Date of Patent: Mar. 3, 2009

(54) SYSTEM AND METHOD FOR FUEL CELL MATERIAL X-RAY ANALYSIS

(75) Inventors: Yuxin Wang, Arlington Heights, IL (US); Wenbing Yun, Walnut Creek, CA (US)

(73) Assignee: Xradia, Inc., Concord, CA (US)

( * ) Notice: Subject to any disclaimer, the term of this patent is extended or adjusted under 35 U.S.C. 154(b) by 60 days.

(21) Appl. No.: 11/619,705

(22) Filed: Jan. 4, 2007

(65) Prior Publication Data

US 2008/0165924 A1 Jul. 10, 2008

(51) Int. Cl.
*G21K 7/00* (2006.01)
(52) U.S. Cl. .............................. 378/43; 378/58; 378/62
(58) Field of Classification Search .................... 378/43, 378/53, 62, 82, 84, 119, 121, 143, 144, 5, 378/46, 57, 58
See application file for complete search history.

(56) References Cited

U.S. PATENT DOCUMENTS 5,222,113 A * 6/1993 Thieme et al. ................ 378/43
5,245,648 A * 9/1993 Kinney et al. ................ 378/43
7,057,187 B1 6/2006 Yun et al. ................ 250/483.1
7,180,981 B2 * 2/2007 Wang ........................ 378/124

OTHER PUBLICATIONS

Brant, M.C., et al., "Electrical and Microstructural Aging of Porous Lanthanum Strontium Manganite/Yttria-Doped Cubic Zirconia Electrodes," Chem. Mater., vol. 13, No. 11, pp. 3954-3961, 2001.
Fujita, K., et al., "Prevention of SOFC Cathode Degradation in Contact with Cr-containing Alloy," Journal of Power Sources, 131, pp. 261-269, 2004.
Tu, Hengyong, et al., "Advances, Aging Mechanisms and Lifetime in Solid-Oxide Fuel Cells," Journal of Power Sources, 127, pp. 284-293, 2004.

* cited by examiner

*Primary Examiner*—Courtney Thomas
(74) *Attorney, Agent, or Firm*—Houston Eliseeva, LLP

(57) ABSTRACT

An imaging technology for fuel cells is based on x-ray microscopy. A metrology system images the electro-chemical interaction areas of solid-oxide fuel cells (SOFC) in-situ. This system takes advantage of both the penetrating power and elemental absorption contrast of hard x-ray radiation to image the internal interaction areas in a SOFC. The technology can further take advantage of the strong dependence of the x-ray absorption on material type and energy to distinguish the four major material types: cathode, electrolyte, air, and low-Z contaminants such as sulfur.

21 Claims, 4 Drawing Sheets

SYSTEM AND METHOD FOR FUEL CELL MATERIAL X-RAY ANALYSIS

BACKGROUND OF THE INVENTION

Fuel cell devices convert chemical energy directly into electrical energy without combustion. The immediate benefit is much higher energy conversion efficiency and the drastic reduction of pollutants. Solid-oxide fuel cells (SOFC), in particular, are able to utilize existing widely used hydrocarbon fuel to simultaneously generate thermal and electrical power with combined heat and power (CHP) efficiency of over 80%. In comparison, internal-combustion engines (ICE) provide 25-30% efficiency with most of the energy loss in the form of exhaust heat and pollution. SOFC technology therefore can significantly reduce the fuel consumption as well as pollutant emission of vehicles, and without the need of exotic fuels.

A critical step in making these devices practical is developing electrode and electrolyte components with high efficiency and high resistance to aging and contamination. The electrochemical reactions occur in a narrow zone along the three-phase boundary (TPB), where the three reaction elements: cathode, solid electrolyte, and gas are in contact. Better electrochemical performances are expected for components with larger TPB length per unit area. Much of SOFC research and development efforts are therefore focused on producing nano-porous structures with maximum TPB length as well as optimizing operating conditions that lead to high performance and corrosion and contamination resistance, e.g. from sulfur.

SUMMARY OF THE INVENTION

A critical tool in the development of SOFC is a three-dimensional imaging technique to visualize and measure the size, distribution, and connectivity of the pores and channels in these nano-porous structures. Furthermore, it is particularly desirable to study the dynamic changes of these structures in-situ and while the device is in operation.

The imaging techniques used today are primarily based on electron microscopy because of their high spatial resolution. But because of the shallow penetration depth of electrons, the imaging processes are generally destructive to the device, as the region of interest (ROI) must be mechanically cross-sectioned to reveal buried structures. This is a tedious and difficult process that is prone to introducing artifacts, particularly with hard and porous ceramic materials used in fuel cells. Furthermore, electron microscopy only provides a surface picture and does not reveal the pore connectivity.

The present invention concerns the use of an imaging technology for fuel cells based on x-ray microscopy. The large penetration depth of x-ray radiation enables imaging through the ROI without sectioning, and when used in combination with the tomography technique used in medical CT scans, the exact three dimensional (3D) structure of a sample can be obtained non-destructively, even while the device is in operation. This technology can further take advantage of the strong dependence of the x-ray absorption on material type and energy to distinguish the four major material types: cathode, electrolyte, air, and low-Z contaminants such as sulfur. This means that that the geometry of porous structures in the TPB can be directly measured from the 3D images to understand a SOFC's electrochemical state and predict its performance. This represents a metrology capability that is important for the development of fuel cell technology. By providing the most direct and relevant information on the exact operating conditions of the device, it has the potential to significantly reduce the development time and improve the reliability.

In one example, a metrology system images the electrochemical interaction areas of solid-oxide fuel cells (SOFC) in-situ. This system takes advantage of both the penetrating power and elemental absorption contrast of hard x-ray radiation to image the internal interaction areas in a SOFC. Combined with computer tomography (CT) technique, the 3D morphology of the interaction volume can be obtained in-situ at 50-nm 3D resolution, and different material compositions can also be determined. Consequently, the exact aging mechanism can be tracked and analyzed dynamically while the device is in operation. This system provides the most direct and relevant information on the exact operating conditions of the device, having the potential to significantly accelerate the development of the SOFC technology and reduce the time-to-market.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The disclosed tool is designed to nondestructively image the three-dimensional structure of the interface area of LSM/YSZ at 1-100 nm resolution while being able to distinguish four different materials: LSM, YSZ, sulfur, and air (empty gap space). There are two important elements to this approach: (1) how to resolve the structures in 3D and (2) how to distinguish different materials.

Figure 1:
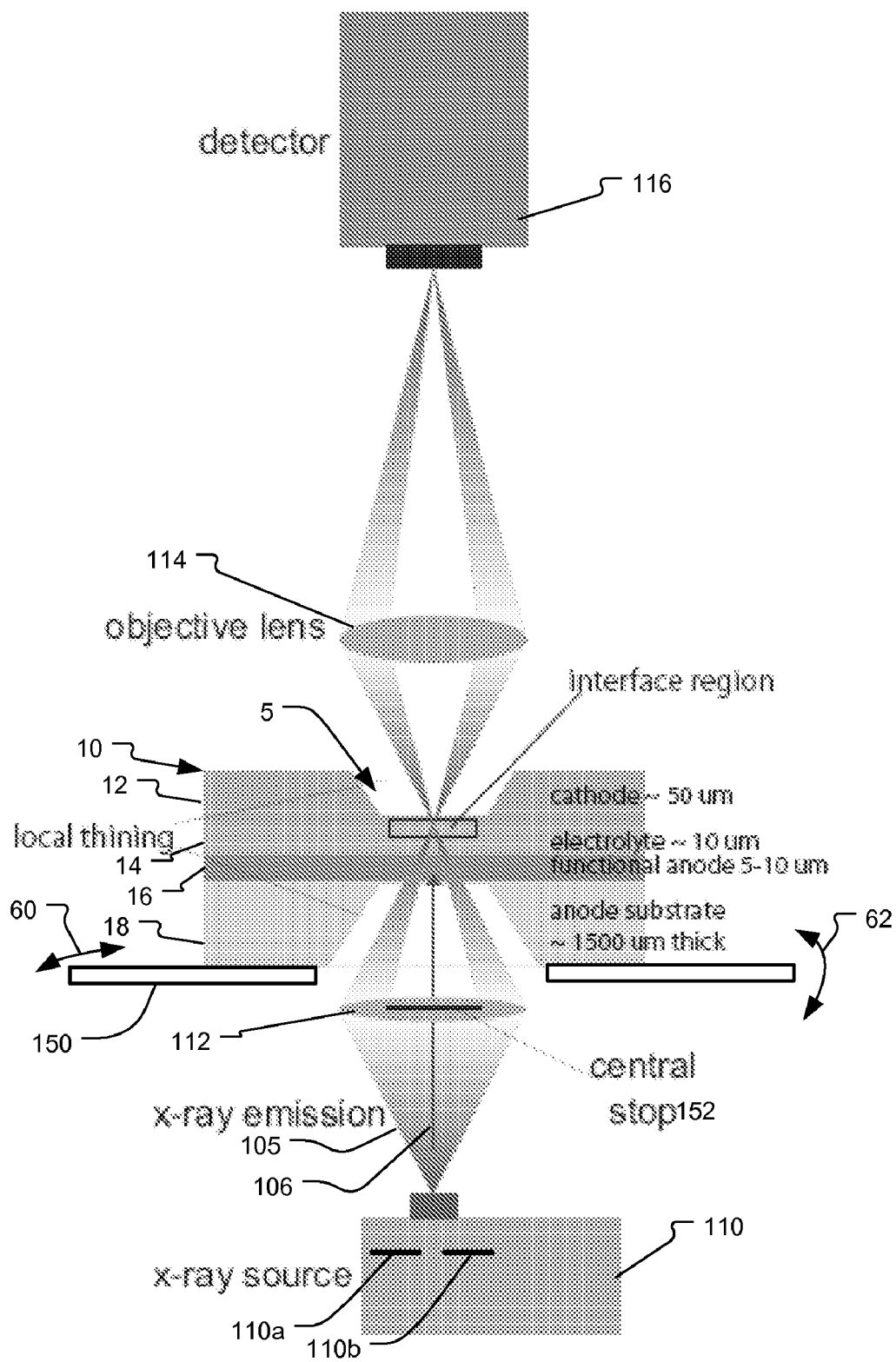
FIG. 1 is a schematic diagram illustrating an x-ray microscope (TXM) according to an embodiment of the present invention.

FIG. 1 shows an x-ray microscope (TXM) 100. In a setup similar to a conventional visible light microscope, x-ray microscope 100 comprises an x-ray source 110, condenser lens 112, objective lens 114, and an area detector system 116. This microscope 100 is used to image a SOFC anode substrate 10. In one example, the anode substrate 10 comprises a cathode layer 12 (thickness approximately 50 micrometers ($\mu$m)), an electrolyte layer 14 (thickness approximately 10 μm), functional anode layer 16 (thickness approximately 5-10 μm), and anode substrate 18 (thickness approximately 1500 μm).

Preferably, a sample stage 150 is used to position the substrate 10 in an x-ray beam 105 from the source propagating along beam axis 106. The rotation stage facilitates tomographic data acquisition by rotating the sample of fuel cell material in a controlled manner. Specifically, the stage 150 rotates the fuel cell material 10 to acquire images at different angles of inclination relative to the axis 106 (see arrow 62) and around axis 106 (see arrow 60) to obtain the multiple projection images needed for tomography data reconstruction.

In the preferred embodiment, the x-ray source 110 is a rotating anode type with molybdenum (Mo) target to generate 17.5 kilo-electron-Volt (keV) x-ray radiation. In other embodiments, the target is copper, silver, or rhodium.

Preferably, the condenser 112 is a capillary reflective lens, and a Fresnel zone plate lens is used as the objective lens 114. A central stop 152 is also preferably provided along the beam axis to block x-ray that will not be or have not been focused by the zone plate lens 114. This improves signal to noise ratio of the system. In one example, the stop is installed on or made part of the condenser 112.

A lens-coupled scintillated CCD camera will be used as the detector 116. In one embodiment, a scintillated CCD camera detector is used similar to that described in U.S. Pat. No. 7,057,187, entitled Scintillator Optical System and Method of Manufacture, which is incorporated herein in its entirety by this reference.

The 17.5 keV x-ray radiation allows samples with 100-200 μm thickness to be imaged. In one example, the anode substrate 18 of the SOFC 10, and also possibly the cathode layer 12, is thinned locally near the region of interest (ROI) 5. A preferred sample preparation procedure is a mechanical process called dimpling that has been used routinely in semiconductor industries to remove the silicon (Si) substrate while keeping the circuitry intact. Skilled operators can routinely use this technique to remove nearly all the substrate while leaving the active circuitry without damage to the delicate interconnects. The materials are removed around the ROI 5, but leaving the active area intact.

Figure 2:
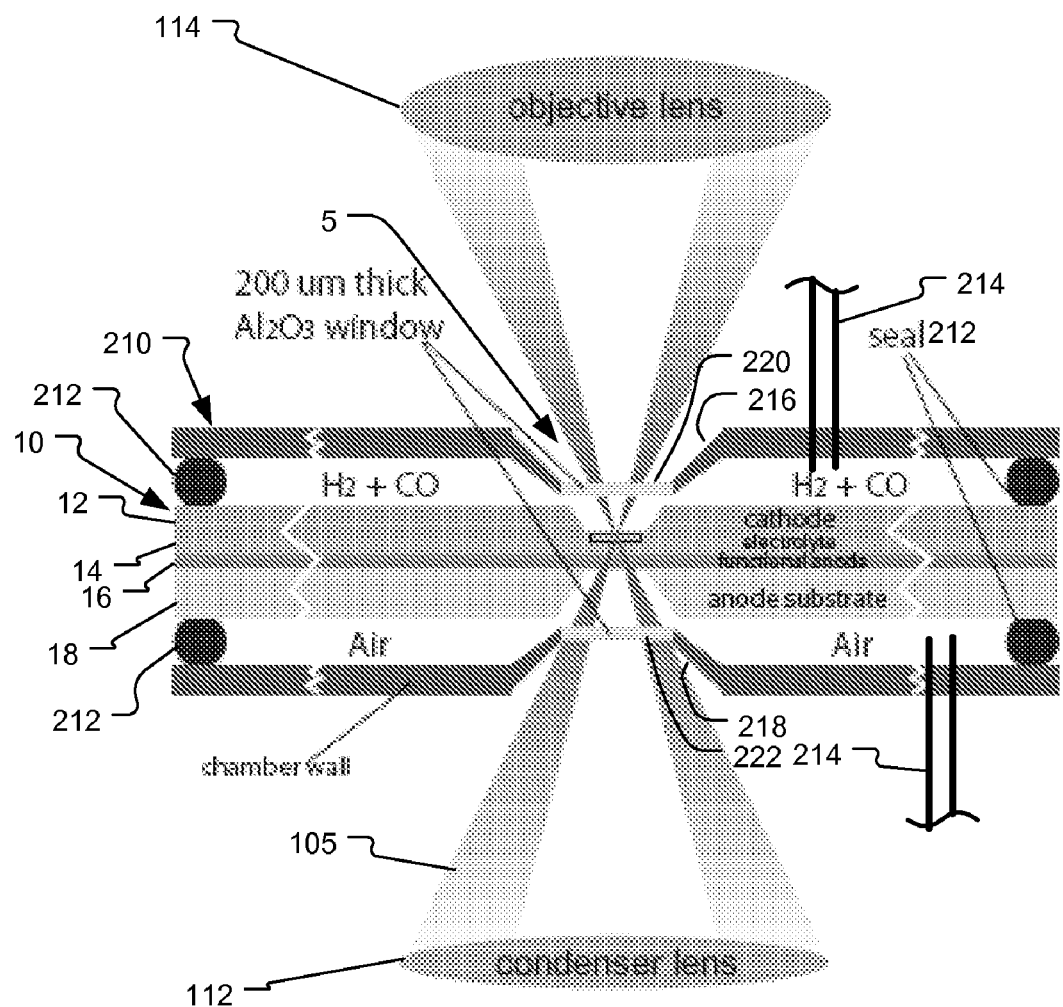
FIG. 2 is a schematic diagram illustrating a microscope sample chamber to image a SOFC device in operation according to an embodiment of the present invention.
Figure 3:
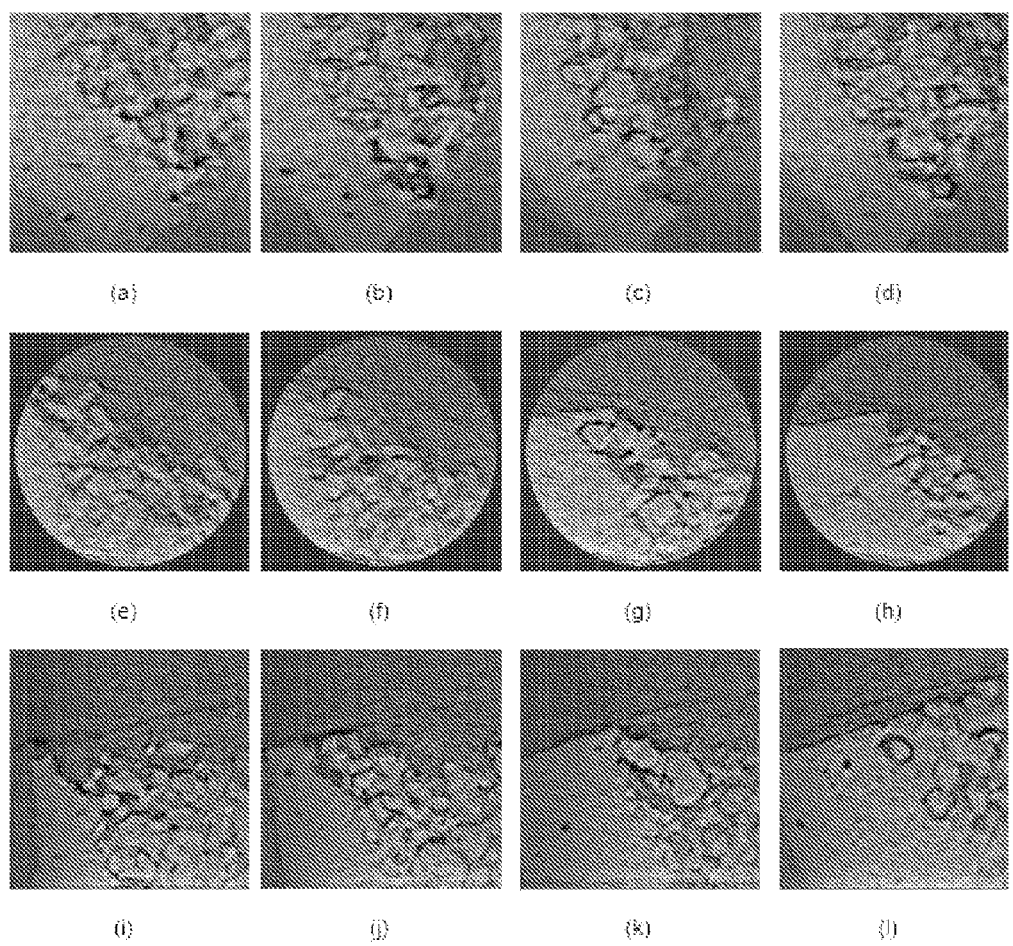
FIG. 3 shows the 3D volume data obtained using the inventive system from a typical SOFC sample shown in virtual cross-sectional views: (a-d) four slices in the different depth direction (perpendicular to imaging beam), (e-h) four slices along the rotation axis (parallel to beam), and (i-l) perpendicular to the previous axes.

As shown in FIG. 2, the preferred embodiment further includes a chamber 210 to facilitate observation of dynamic changes of the TPB in situ. The chamber 210 functions to enable the SOFC device 10 to operate normally and also allows the imaging x-ray beam 105 to pass through. It is essentially a standard test chamber for planar SOFC devices modified with one or two x-ray windows.

The test chamber 210 has seals 212 to isolate the two sides of the device. It also has gas feed-through tubes to inject and remove fuel air and exhaust gases, heaters to start the electrochemical reaction, electrodes to draw electric power, and measuring devices 214. Upper and lower cone-shaped windows devices 216, 218 are provided, each made from a thin metallic or ceramic membrane. Using hard x-ray radiation with 17.5 keV energy, there is a wide choice of window materials with acceptable absorption for the upper and lower window elements 220, 222 at the peaks of the fustoconical window devices 216, 218. For example, 200 μm thick sapphire (Al2O3) provides about 80% transmission and are commercially available.

The objective lens 114 of this imaging system 100 is preferably a zone plate lens that focuses electromagnetic radiation by diffraction, as opposed to the refraction effect used by glass lens for focusing visible light. It is essentially a circular diffraction grating with the grating period decreasing towards the periphery. With this arrangement, the diffraction angle increases with the increasing radius, and all radiation passing through the zone plate converges to a focal point. The diffraction-limited resolution of a zone plate measured by the Rayleigh criterion is simply 1.22 times the width of the outer-most grating line, or the outermost zone width. The focal length of a zone plate is expressed as $f=DDr/l$, where is $D$ the diameter, $Dr$ is the outer-most zone width, and $l$ is the wavelength. The numerical aperture is $NA=l/2Dr$. For example, in order to achieve the 60 nanometer (nm) resolution, a zone plate lens with an outermost zone width of 50 nm is preferred.

The depth of field (DOF) is generally defined as twice the resolution divided by the numerical aperture. Here, DOF is about 200 μm. Therefore a region of interest with 100-200 μm is contained completely within the DOF. In other words, all structures in the region of interest are imaged with 60 nm resolution and there is no defocus effect.

The volume of the ROI 5 is a region having a thickness of a few micrometers and extends over the area of the SOFC. One typically needs to image a 20 μm×20 μm sample area per measurement. A computed tomography (CT) technique is used to study the 3D structures of the interface area between the cathode 12 and the electrolyte 14, or the anode 18. The TPB is then identified from the 3D image and the effected interaction length can be measured.

A computed tomography (CT) algorithm originally developed in the medical imaging community can resolve these features in depth. In the imaging system shown in FIG. 1, the x-ray beam passes through the sample to record an image containing all features that overlap in the depth direction. With tomography imaging process, the sample is imaged at different view angles to acquire a series of tomographic projections, and these projections are then mathematically back-projected into a volume data to form a 3D representation of the object. The features in the sample 10 can then be analyzed by studying the data volume. Typical techniques used in the analysis include studying the cross-sectional views of the volume, or virtual sectioning (see FIGS. 3a-l), as is most often used in medical imaging applications, and studying the volume rendering. This is done without physically modifying the object, while in contrast, to obtain equivalent cross-section views with SEM, one must physically cut and section the sample through the region of interest—a completely destructive process. In the medical imaging analogy, the TXM is compared with non-invasive imaging methods such as CT or MRI while SEM imaging can be compared to the invasive procedures such as biopsy or exploratory surgery. And their applications should comparable as well: the non-invasive imaging method should be used as the first screening or diagnosis procedure, while the invasive methods applied when the non-invasive methods cannot provide a definite answer.

A typical result from a planar SOFC sample is shown in FIGS. 3a-l. These results were acquired using 8.05 keV x rays generated from a rotating anode x-ray source with a copper (Cu) target rather than the 17.5 keV preferred design. Its objective lens was a zone plate lens with 50 nm outer most zone width with theoretical maximum resolution of 60 nm. A scintillator coupled CCD camera with 1024×1024 pixels was used as the detector. The substrate of the SOFC sample was thinned to a wedge shape.

The reconstructed 3D structure is shown in FIGS. 3a-l with 4 slices along each of the 3 axes: (a-d) in the depth direction, where the slices are perpendicular to the imaging beam direction $z$; (e-h) in the rotation axis direction $y$ (images parallel to the beam); and (i-l) along $x$ x axis perpendicular $y$-$z$ plane. The TPB can be easily identified from the image, and furthermore, the interaction length of the TPB can be measured from these images or from the 3D volume, for example automatically with specialized software. Furthermore, this measurement is made non-destructively and at about 2 centimeter (cm) stand-off working distance, the 3D images can also be made with a device in operation.

Figure 4:
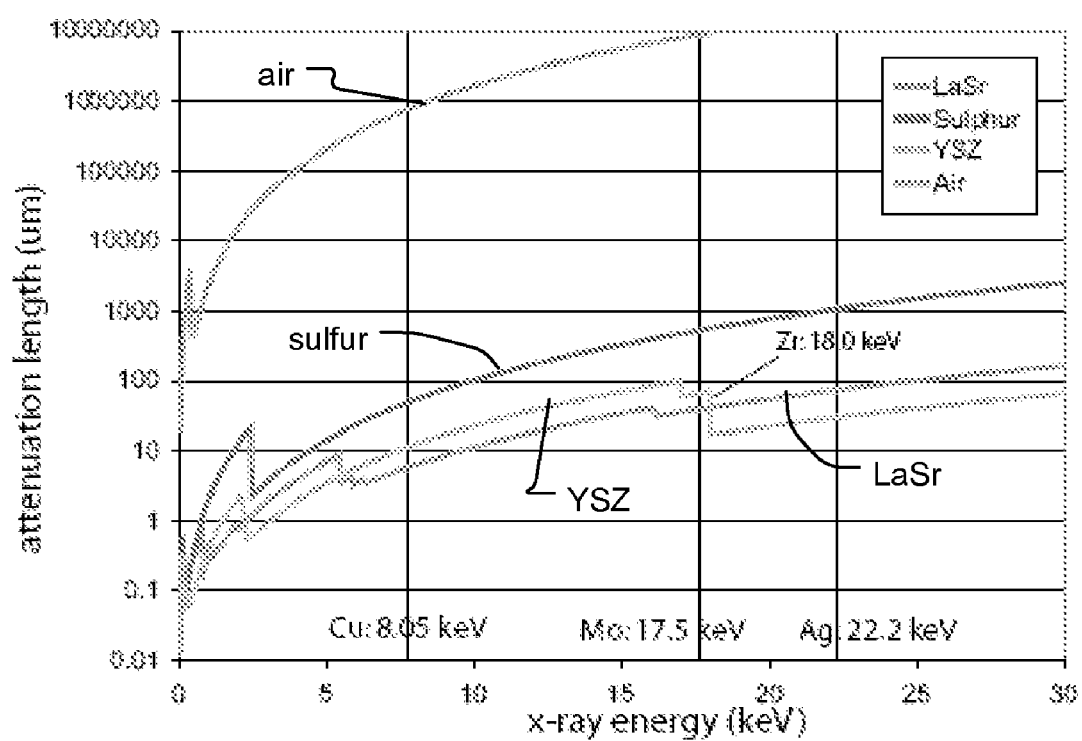
FIG. 4 is a plot of 1/e attenuation length of bulk LSM, YSZ, sulfur, and air as a function of x-ray energy.

An important advantage of x-ray microscopy is that the absorption depends strongly on the elemental composition and x-ray energy. Thus, different materials can be distinguished as summarized in FIG. 4 where the l/e attenuation lengths of LSM, YSZ, Sulfur, and air are plotted as a function of x-ray energy. Air is practically transparent with this combination of x-ray energy range and length scale. Note that the attenuation length for all three solid materials increases with the x-ray energy and the use of higher energy x rays allows thicker samples to be imaged. For example, the images from the preliminary experiments were acquired using 8.05 keV x rays. This requires the sample to be thinned to about 20 μm at the region of interest. However, a system using 17.5 keV x rays from Mo emission will allow a region of interest to remain in 100-200 μm thickness, thus greatly simplifying the sample preparation process and furthermore allowing observation at native operating conditions.

At 17.5 keV, the attenuation of LSM ($La_{1-x}Sr_xMnO_{3-\delta}$), YSZ ($La_{0.65}Sr_{0.3}MnO_{3-\delta}$), and sulfur differ considerably. For example, with nearly half the attenuation length, LSM is more than twice more absorbing than YSZ, thus producing twice the image contrast. The two materials can then be identified in the 3D image from their very different absorptive properties, for example with a simple threshold. Air is practically transparent at this energy. It can be distinguished from both LSM and YSZ as empty space, while the solid materials can be distinguished from each other by their different pixel density. With this method, the three-dimensional structures of all three materials in the region where the electro-chemical reaction take place can be identified from a 3D image. This gives the ability to study the TPB from the 3D data without physically altering the sample through destructive processes.

Because of strong absorption edges of Y and Zr at 17.1 keV and 18 keV, there is actually a contrast reversal at x-ray energies above 18 keV. For example, at silver emission line at 22 keV, YSZ actually becomes about three times more absorbing than LSM. This means that when two images are taken, one using a Mo source with 17.5 keV emissions and one with Ag source with 22 keV emissions, the YSZ material will appear more absorbing than LSM in the first image, but their contrast will reverse in the second image.

In one embodiment, the x-ray source 110 of FIG. 1, comprises two separate sources, or a single source with two different target materials 110a, 110b. The data obtained with emissions at the two energies are then combined to increase the accuracy of the material identification. This ability to map different materials in 3D not only provides new and unique capability for studying the TPB of SOFC sample, it also provides a powerful tool for materials science research in general.

While this invention has been particularly shown and described with references to preferred embodiments thereof, it will be understood by those skilled in the art that various changes in form and details may be made therein without departing from the scope of the invention encompassed by the appended claims.

What is claimed is:

1. A system for imaging structures of fuel cells, comprising:
   an x-ray source for generating x rays;
   a sample stage for holding fuel cell material;
   a chamber for containing the fuel cell material;
   an x-ray objective lens for collecting and focusing the x-rays passing through the fuel cell material; and
   a detector for detecting the x-rays from the x-ray lens.

2. A system claimed in claim 1, wherein the fuel cell material is mounted on a rotation stage to facilitate tomographic data acquisition.

3. A system claimed in claim 2, where fuel cell material is rotated by the rotation stage to acquire images at different rotation angles to obtain projection images needed for tomography data reconstruction.

4. A system claimed in claim 1, wherein the x-ray source comprises an electron source for generating an electron beam directed at a metal anode target, the electron beam generating x-rays in the metal layer.

5. A system claimed in claim 4, wherein the anode comprises copper.

6. A system claimed in claim 4, wherein the anode comprises molybdenum.

7. A system claimed in claim 4, wherein the source is a source system comprising two or more different targets for generating x-rays at different energy levels.

8. A system claimed in claim 7, wherein one of the targets is copper and another is molybdenum.

9. A system claimed in claim 1, wherein the chamber contains the fuel cell material along with fluids or gases enabling the fuel cell material to operate to convert chemical energy directly into electrical energy.

10. A system claimed in claim 9, wherein the chamber comprises one or more window structures through which the x-ray pass to access a region of interest of the fuel cell material.

11. A system claimed in claim 9, further comprising two window structures on either side of the chamber, the x-rays being directed to pass through the two window structures on the path between the x-ray source and the detector.

12. A system claimed in claim 9, further comprising fuel and exhaust tubes to the chamber for providing fuel to the fuel cell and removing exhaust from the fuel cell during the detection of the x-rays by the detector.

13. A system claimed in claim 1, wherein the source comprises an electron source for generating an electron beam directed at two or more metal anode targets, the electron beam generating x-rays in metal layers of the targets to generate x-rays at different energy levels, combining image data from the different energy levels to identify materials in the fuel cell.

14. A method for imaging fuel cells, comprising:
   generating x rays;
   holding fuel cell material in the x rays;
   collecting and focusing the x-rays passing through the fuel cell material; and
   detecting the collected and focused x-rays from the fuel cell material to form an image.

15. A method claimed in claim 14, further comprising rotating the fuel cell material while acquiring images at different rotation angles to obtain projection images for tomography data reconstruction.

16. A method claimed in claim 14, further comprising providing one or more windows structures through which the x-ray pass to access a region of interest of the fuel cell material.

17. A method claimed in claim 16, further comprising rotating the fuel cell material while acquiring images at different rotation angles while the fuel cell material is converting chemical energy directly into electrical energy to obtain projection images for tomography data reconstruction.

18. A method claimed in claim 14, further comprising operating the fuel cell material to convert chemical energy directly into electrical energy while detecting the x-rays to generate images of the operating fuel cell.

19. A method claimed in claim 14, further comprising providing two window structures on either side of the chamber, the x-rays being directed to pass through the two window structures on path through the fuel cell material.

20. A method claimed in claim 14, further comprising piping fuel and exhaust to and from the fuel cell during the detection of the x-rays to generate images of the operating fuel cell.

21. A method claimed in claim 14, wherein generating the x-rays comprises generating an electron beam directed at two or more metal anode targets, the electron beam generating x-rays in metal layers of the targets to generate x-rays at different energy levels, and the method further comprises combining image data from the different energy levels to identify materials in the fuel cell.

* * * * *